US008852278B2

(12) United States Patent
Bellas

(10) Patent No.: US 8,852,278 B2
(45) Date of Patent: Oct. 7, 2014

(54) LATERAL CAGE WITH INTEGRATED PLATE

(75) Inventor: Jonathan Bellas, Raynham, MA (US)

(73) Assignee: DePuy Synthes Products, LLC, Raynham, MA (US)

( * ) Notice: Subject to any disclaimer, the term of this patent is extended or adjusted under 35 U.S.C. 154(b) by 239 days.

(21) Appl. No.: 13/364,282

(22) Filed: Feb. 1, 2012

(65) Prior Publication Data

US 2013/0166027 A1  Jun. 27, 2013

Related U.S. Application Data

(60) Provisional application No. 61/579,567, filed on Dec. 22, 2011.

(51) Int. Cl.
A61F 2/44 (2006.01)

(52) U.S. Cl.
USPC .................................... 623/17.11; 623/17.16

(58) Field of Classification Search
USPC .................... 623/17.11–17.16; 606/246–249
See application file for complete search history.

(56) References Cited

U.S. PATENT DOCUMENTS

| 6,432,106 | B1 | 8/2002 | Fraser |
| 6,695,846 | B2 | 2/2004 | Richelsoph |
| 6,890,335 | B2 | 5/2005 | Grabowski |
| 7,112,222 | B2 | 9/2006 | Fraser |
| 7,288,094 | B2 | 10/2007 | Lindemann |
| 7,288,095 | B2 | 10/2007 | Baynham |
| 7,306,605 | B2 | 12/2007 | Ross |
| 7,341,590 | B2 | 3/2008 | Ferree |
| 7,438,715 | B2 | 10/2008 | Doubler |
| 7,594,931 | B2 | 9/2009 | Louis |
| 7,641,665 | B2 | 1/2010 | Zubok |
| 7,674,279 | B2 | 3/2010 | Johnson |
| 7,704,255 | B2 | 4/2010 | Michelson |
| 7,862,616 | B2 | 1/2011 | Lechmann |
| 7,875,062 | B2 | 1/2011 | Lindemann |
| 7,887,595 | B1 | 2/2011 | Pimenta |
| 8,002,808 | B2 | 8/2011 | Morrison |
| 8,007,523 | B2 | 8/2011 | Wagner |

(Continued)

FOREIGN PATENT DOCUMENTS

WO  WO 2009025841  2/2009
WO  WO 2011080535  7/2011

OTHER PUBLICATIONS

Search Report and Written Opinion dated Apr. 11, 2013 from corresponding PCT/US2012/070082.

*Primary Examiner* — Pedro Philogene
*Assistant Examiner* — Christina Negrellirodrigue
(74) *Attorney, Agent, or Firm* — Raymond N. Scott, Jr.

(57) ABSTRACT

An intervertebral fusion cage having a plate pivotally attached thereto. The plate and cage are pivotally coupled but move independently of each other. The plate is made up of two smaller plate halves: a superior plate half and an inferior plate half. Both plate halves form the larger plate. The plates are joined using a cross pin that provides a pivot point about which the plate halves rotate. The same pin also joins the plate halves to the cage, thus allowing the plate halves to pivot about the cage. It is believed that the device of the present invention will reduce the difficulties in placing a lateral plate down a port and manipulating it into position. Mating the plate to the cage will reduce the chances of micromotion and improve fusion rate, resulting in improved patient outcomes.

17 Claims, 17 Drawing Sheets

(56) References Cited

U.S. PATENT DOCUMENTS

| | | |
|---|---|---|
| 2006/0241597 A1* | 10/2006 | Mitchell et al. ............... 606/61 |
| 2006/0247650 A1* | 11/2006 | Yerby et al. ................... 606/90 |
| 2007/0049941 A1 | 3/2007 | Thramann |
| 2007/0233118 A1 | 10/2007 | McLain |
| 2008/0294262 A1 | 11/2008 | Levieux |
| 2008/0300634 A1 | 12/2008 | Gray |
| 2010/0004747 A1 | 1/2010 | Lin |
| 2010/0016901 A1 | 1/2010 | Robinson |
| 2010/0042159 A1 | 2/2010 | Butler |
| 2010/0249937 A1* | 9/2010 | Blain et al. ................ 623/17.16 |
| 2010/0292696 A1 | 11/2010 | Chantelot |
| 2010/0292737 A1 | 11/2010 | Suh |
| 2010/0305704 A1 | 12/2010 | Messerli |
| 2011/0008864 A1 | 1/2011 | Deinhammer et al. |
| 2011/0009908 A1 | 1/2011 | Ferguson |
| 2011/0015745 A1* | 1/2011 | Bucci ....................... 623/17.16 |
| 2011/0082550 A1 | 4/2011 | Yeh |
| 2011/0106159 A1 | 5/2011 | Nazeck |
| 2011/0184415 A1 | 7/2011 | Anderson |
| 2011/0213421 A1 | 9/2011 | Binder |
| 2011/0251689 A1 | 10/2011 | Seifert |

* cited by examiner

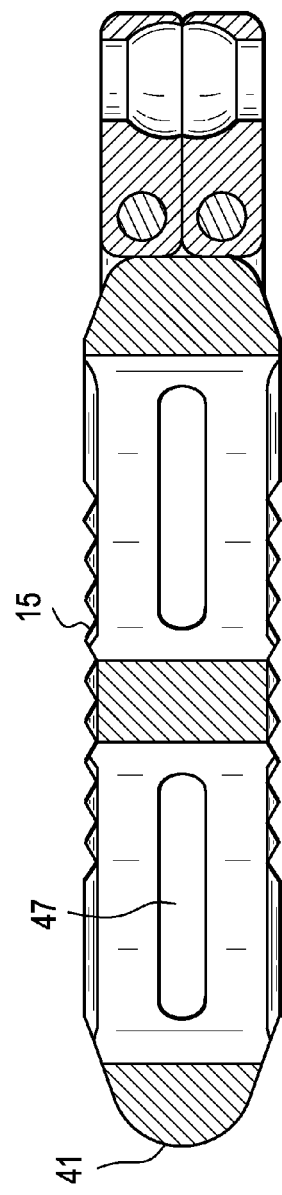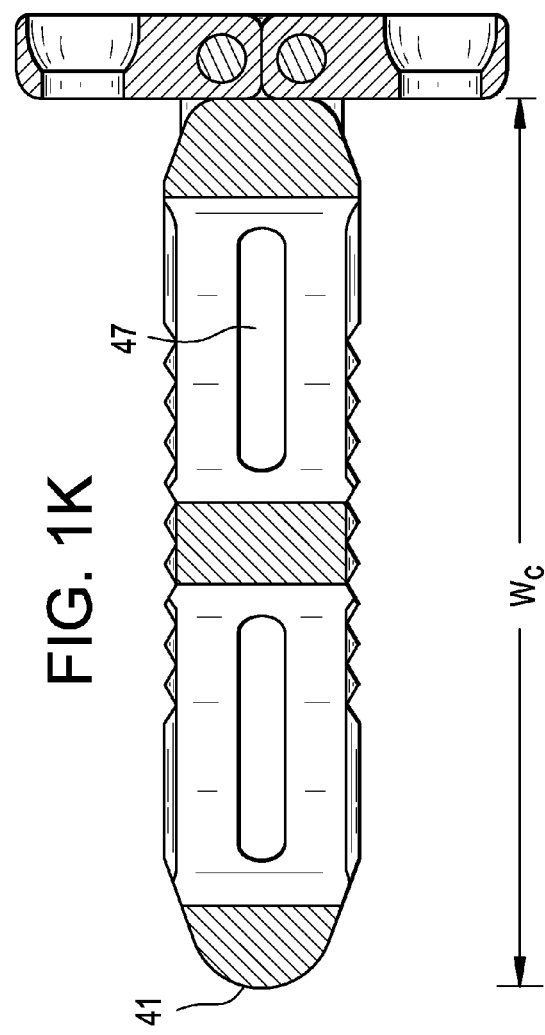

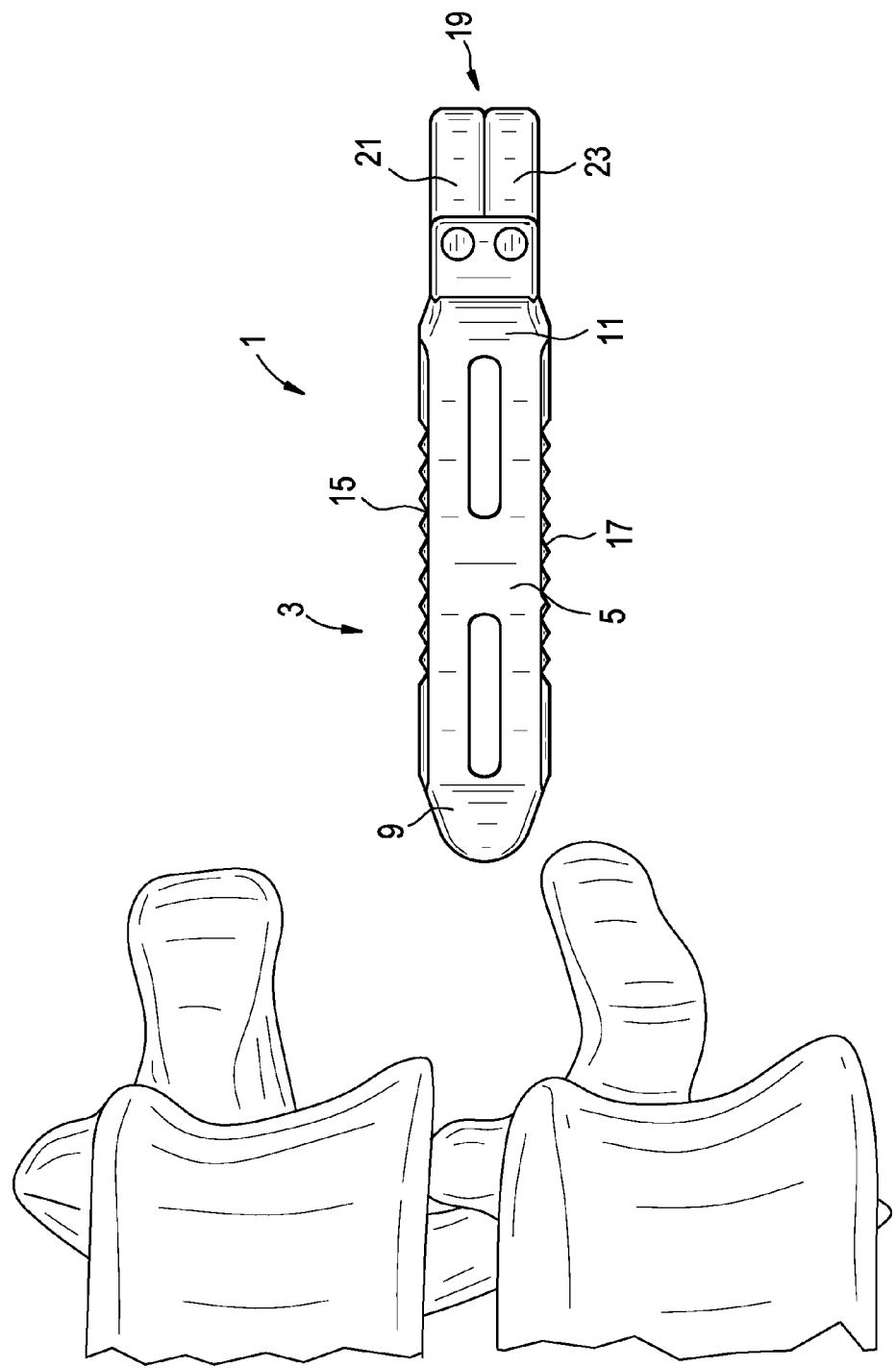

LATERAL CAGE WITH INTEGRATED PLATE

This application claims priority from U.S. Ser. No. 61/579,567, filed on Dec. 22, 2011, and entitled "Lateral Cage with Integrated Plate" (DEP6432USPSP), the specification of which is incorporated by reference in its entirety.

BACKGROUND OF THE INVENTION

A lateral access approach is frequently selected to deliver interbody fusion cages to the lumbar spine. In comparison to conventional anterior or posterior approaches to the lumbar spine, the lateral approach is thought to minimize posterior and/or anterior tissue damage as well as reduce surgery time, associated blood loss, vascular damage and infection risk.

In general, it is known in the art to mount a lateral fusion cage with a plate that secures the cage to the sides of adjacent vertebral bodies.

U.S. Pat. No. 7,594,931 (Louis) discloses an intervertebral arthrodesis implant for insertion in an intervertebral space separating opposite faces of two adjacent vertebrae. The implant has a ring-shaped intervertebral cage having a bar that extends perpendicular to the axis of the spine. The bar has a height less than the rest of the cage. A surface of the cage contacting the vertebrae has an undulating shape for limiting sliding of the cage in a plane parallel to the vertebral faces.

PCT Published Patent Application WO2011-080535 (Dinville) discloses anchoring devices, anchoring systems for intervertebral implants, intervertebral implants, and instruments and methods for implanting the implants. In preferred configurations, these various objects share the feature of comprising or cooperating with an anchoring device having a body comprising at least one curved plate elongated along a longitudinal axis. The plate is designed to be inserted through a passage crossing at least a part of the implant in order to penetrate into at least one vertebral endplate and attach this implant onto this vertebral endplate by means of at least one stop retaining the implant. The body of the anchoring device comprises at least one longitudinal rib on at least a part of at least one of its faces, the rib being designed to cooperate with a groove made in a passage of implant.

In one type of intervertebral device suited for the lateral approach, the fusion cage is mounted with a plate that secures the cage to the adjacent vertebral bodies. In particular, US Published Patent Application 2010-0004747 (Lin) discloses a spinal fixation device comprising a trans-vertebral and intravertebral plate and a rectangular cage with a slot for the plate for neutralizing intervertebral movement in spinal interbody fusion. The rectangular cage with a vertical or oblique slot is inserted into the intervertebral space from the lateral or anterior side of the spinal column. The plate is then inserted through the slot of the cage and hammered into and buried inside the two adjacent vertebral bodies to achieve three-dimensional intervertebral fixation.

SUMMARY OF THE INVENTION

The present inventor has noted that, in the lateral cage-with-plate device disclosed by Lin, the orientation of the plate during insertion produces a relatively large profile, extending far above and below the height of the disc space, thereby detracting from the minimally invasive, tissue-sparing nature of the lateral approach.

The present invention seeks to provide a lateral cage-with-plate device that can be inserted in a minimally invasive manner, preferably through a portal such as a tube.

The present invention relates to an intervertebral fusion cage having a plate pivotally attached thereto. The plate and cage are pivotally coupled but move independently of each other.

The plate is made up of two smaller plate-halves: a superior plate half and an inferior plate half. Together, both plate halves form the larger plate. One or two cross pins also join the plate halves to the cage, thus allowing the plate halves to pivot about the cage. In one embodiment, the plates are joined to each other using the cross pin. Each plate half can have one or more throughholes passing therethrough. Typically, a first throughhole is present at a first end of the plate half and may traverse the plate depth (i.e., it runs in the anterior-posterior direction). The above-mentioned cross pin passes through this first throughhole and thereby pivotally connects the plate half to the cage. A second throughhole may be present at a second end of the plate half and run transverse to the first throughhole. It runs in the frontal plane and may traverse the plate width. Through this second throughhole, the surgeon may pass a bone screw in order to secure the plate half to the adjacent vertebral body.

Due to the pivoting nature of the plates, the device of the present invention has two configurations: an open configuration and a closed configuration. In the closed configuration, the plate halves-are adjacent each other and run in the medial-lateral axis of the cage. This configuration has a small profile and so is amenable to insertion through a portal. The open configuration projects the plate halves perpendicularly to the cage (spanning the height of the cage) and so can accept screws for fixation to adjacent vertebral bodies.

It is believed that, owing to its small insertion profile, the device of the present invention will encounter fewer difficulties when it is placed down a portal and its plate is manipulated into position. Mating the plate to the cage will reduce the chances of micromotion and improve fusion rates, resulting in improved patient outcomes. As compared to the Lin plate, the device of the present invention also reduces the stretching of the psoas muscle during implantation, resulting in reduced post-operative complications.

Further, the rotational freedom of this device will allow for fixation with variable plate angles to adjust to the patient's anatomy.

Therefore, in accordance with the present invention, there is provided an intervertebral fusion device comprising:

a) an intervertebral fusion cage having an anterior wall, a posterior wall, first and second side walls connecting the anterior and posterior walls to form a central throughhole, an upper surface adapted for gripping an upper endplate and a lower surface adapted for gripping a lower endplate;

b) a plate comprising first and second halves, wherein each half of the plate is pivotally connected to the cage.

DESCRIPTION OF THE FIGURES

FIGS. 1a-1k discloses various views of the device of the present invention

FIGS. 2a-2i disclose the device of the present invention at various stages of insertion into a disc space.

DETAILED DESCRIPTION OF THE INVENTION

Figure 1A:
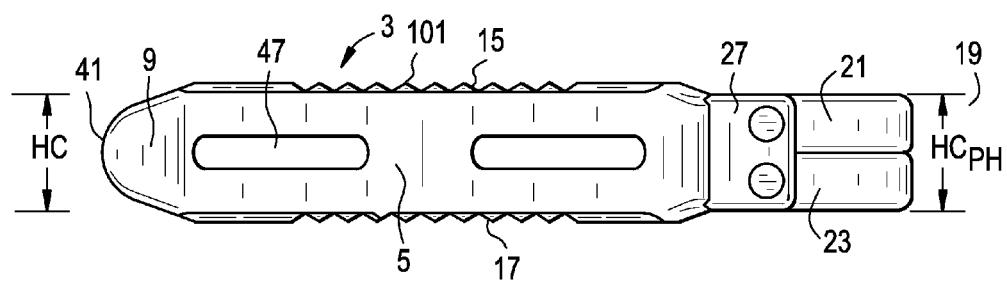
Figure 1B:
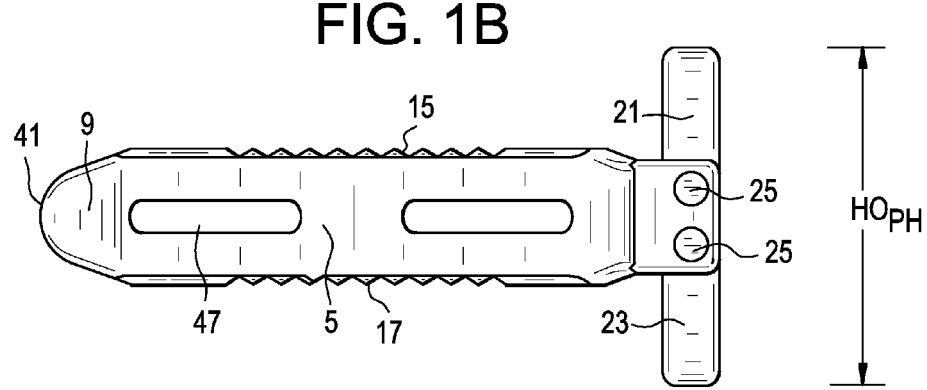
Figure 1C:
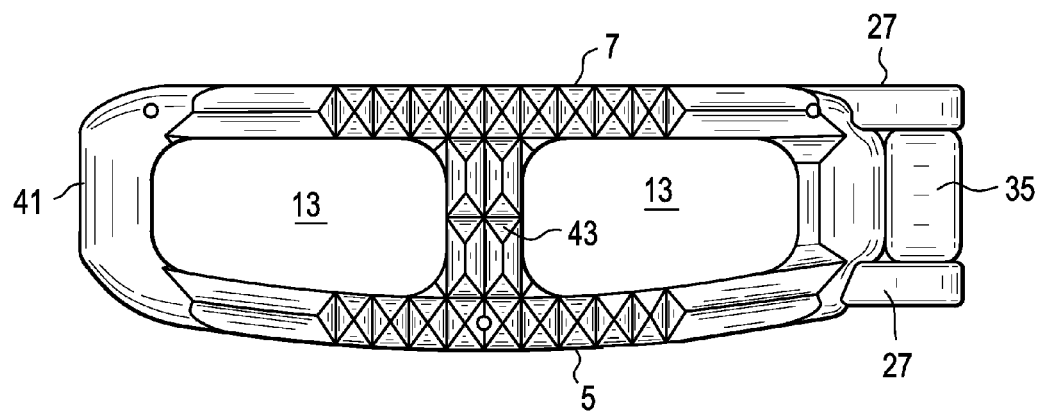
Figure 1D:
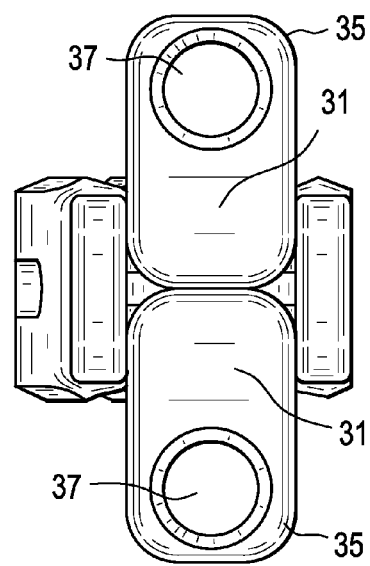
Figure 1E:
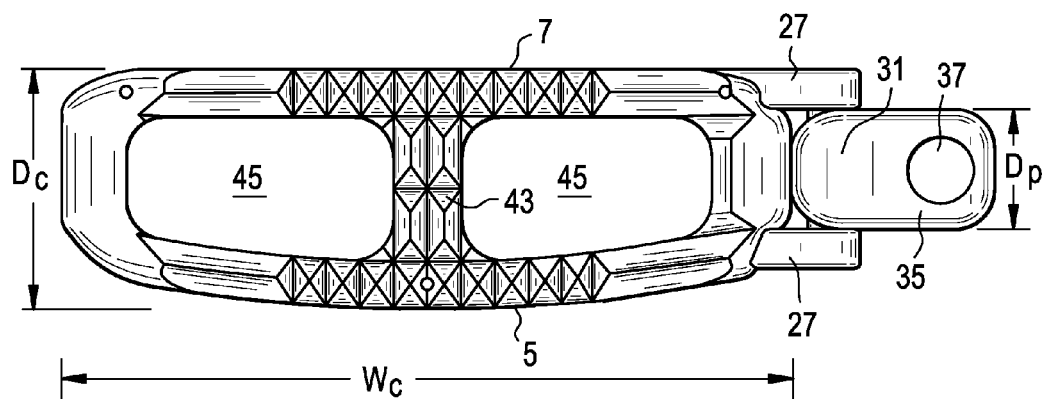
Figure 1F:
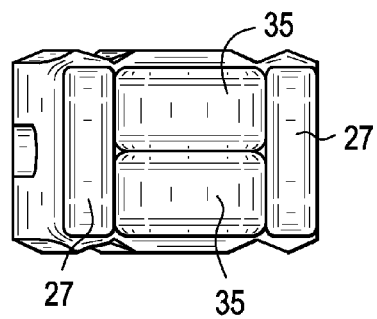
Figure 1G:
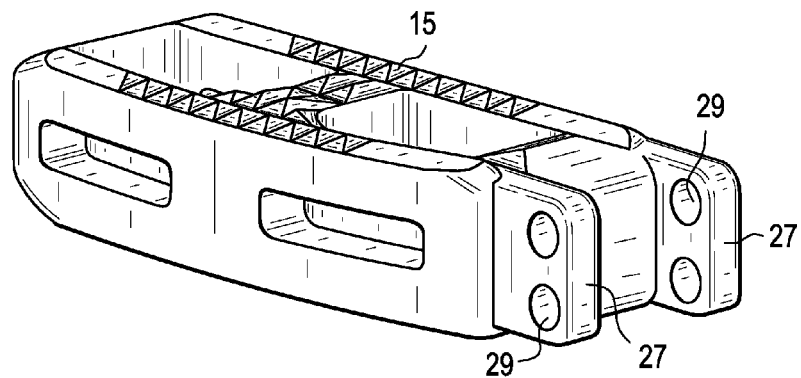
Figure 1H:
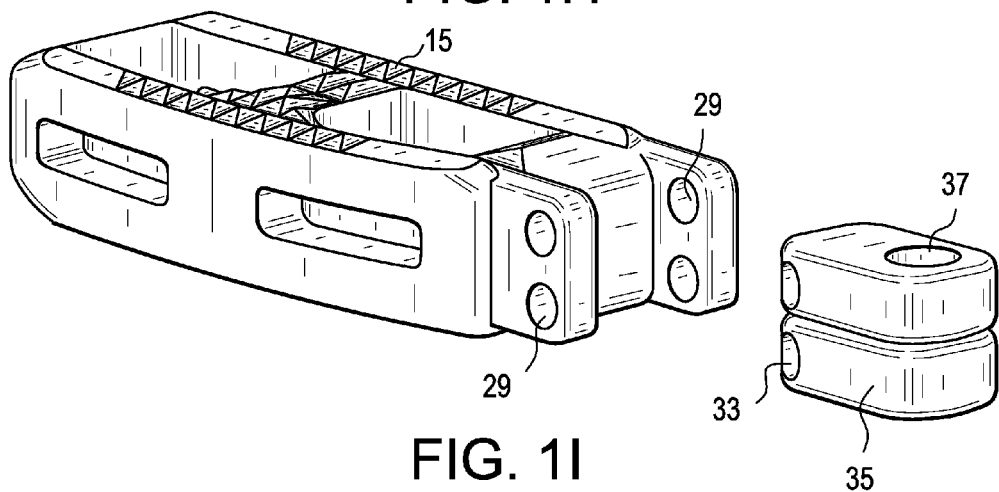
Figure 1I:
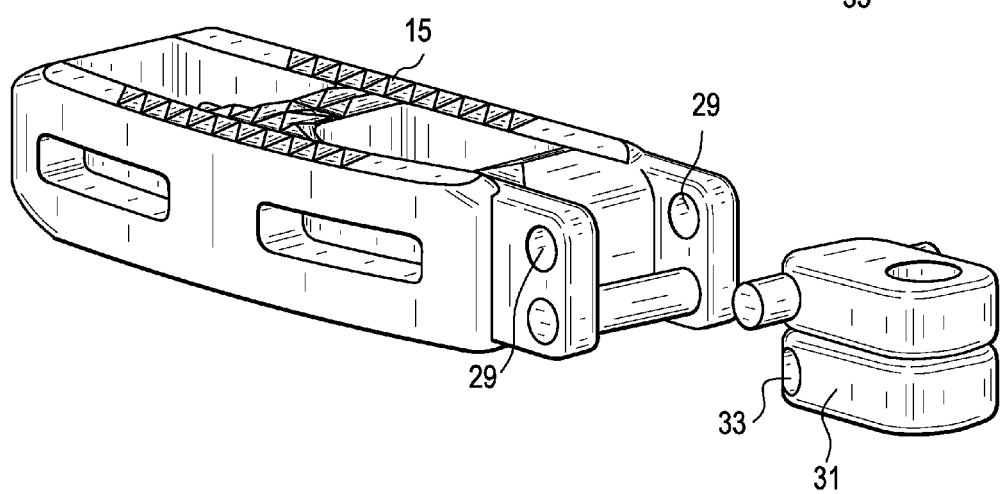

Now referring to FIGS. 1a-4c, there is provided an intervertebral fusion device 1 comprising:
a) an intervertebral fusion cage 3 having an anterior wall 5, a posterior wall 7, first 9 and second 11 side walls connecting the anterior and posterior walls to form a central throughhole 13, an upper surface 15 adapted for gripping an upper endplate and a lower surface 17 adapted for gripping a lower endplate;
b) a plate 19 comprising first 21 and second 23 halves, wherein each half of the plate is pivotally connected to the cage.

In some embodiments, the device further comprises c) a cross pin 25, wherein the cage further comprises a pair of flanges 27 extending from the same sidewall of the cage, each flange having a throughhole 29, wherein the flange throughholes are aligned, wherein the first and second half of the plate each has a first end portion 31 having a throughhole 33, wherein the throughholes of each plate half are aligned, and wherein the pin passes through the througholes of the flanges and the throughholes of the plate halves. This cross pin allows for the pivoting of the plates about the cage in the frontal plane.

In some embodiments, the device of the present invention comprises a plurality of cross pins. This embodiment is shown in FIG. 1a-1k, which has two cross pins. In this embodiment, each flange has two through-holes 33. Thus, the device may further comprise:
c) first and second pins,
wherein the cage further comprises a pair of flanges, each flange having a first and second throughhole, wherein the first throughholes are aligned and wherein the second throughholes are aligned, wherein the first and second plate halves each has a first end portion having a throughhole,
wherein the first pin passes through the first througholes of the flanges and the throughhole of the first plate half.
wherein the second pin passes through the second througholes of the flanges and the throughhole of the second plate half.

Figure 2B:
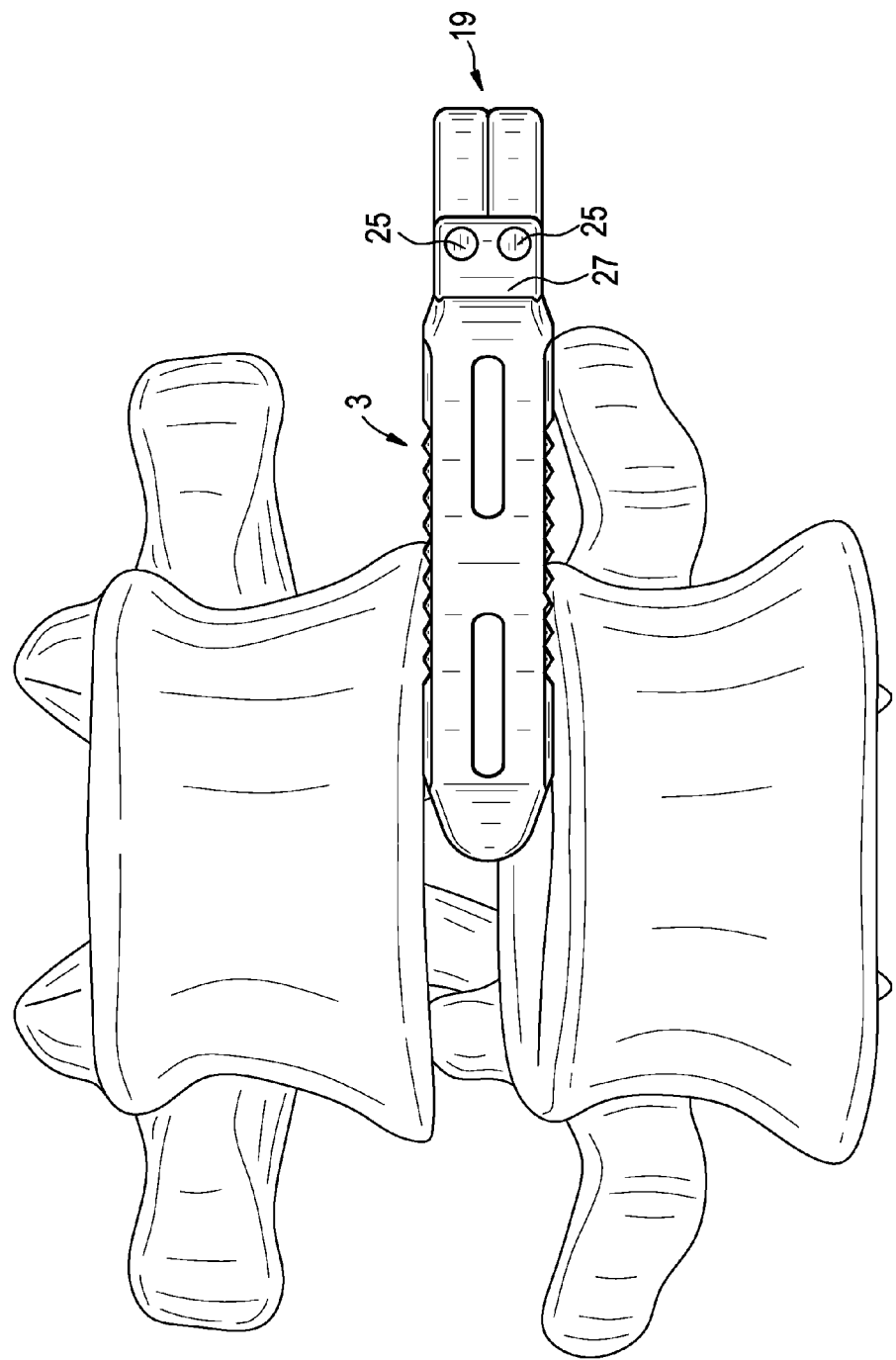
Figure 2C:
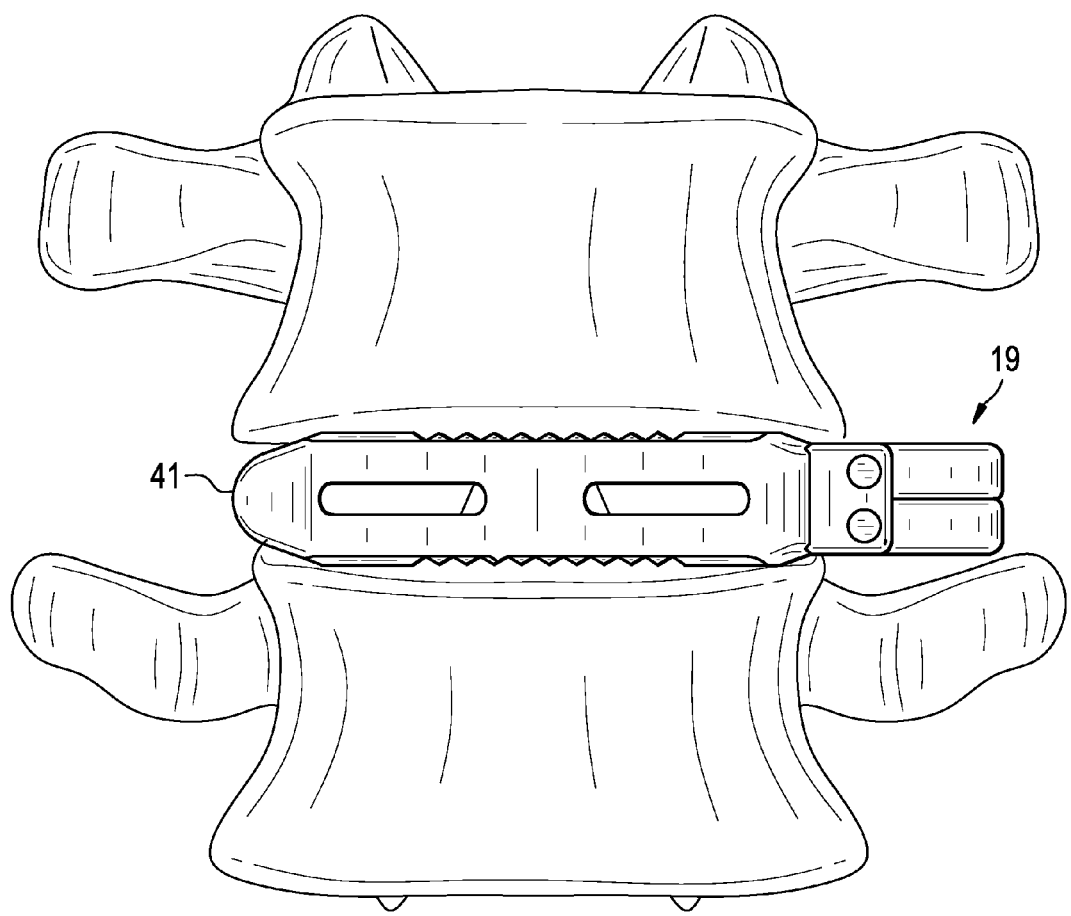
Figure 2D:
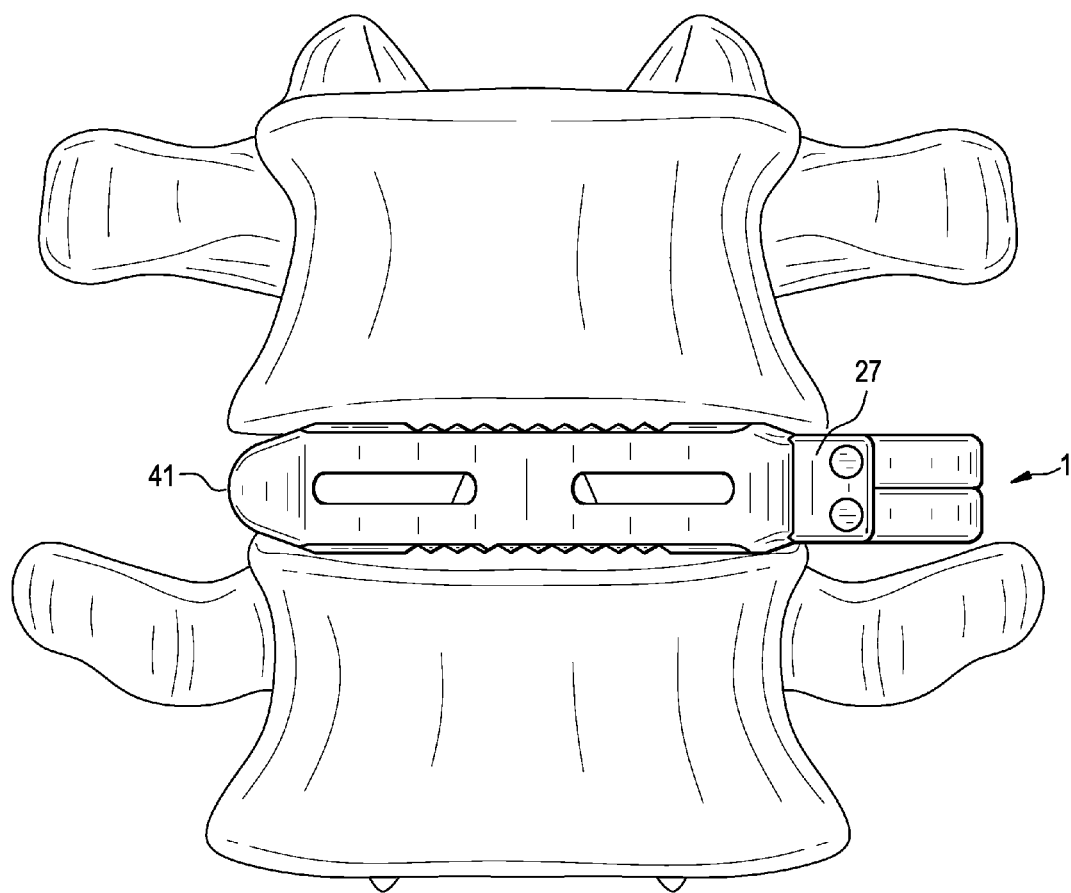
Figure 2E:
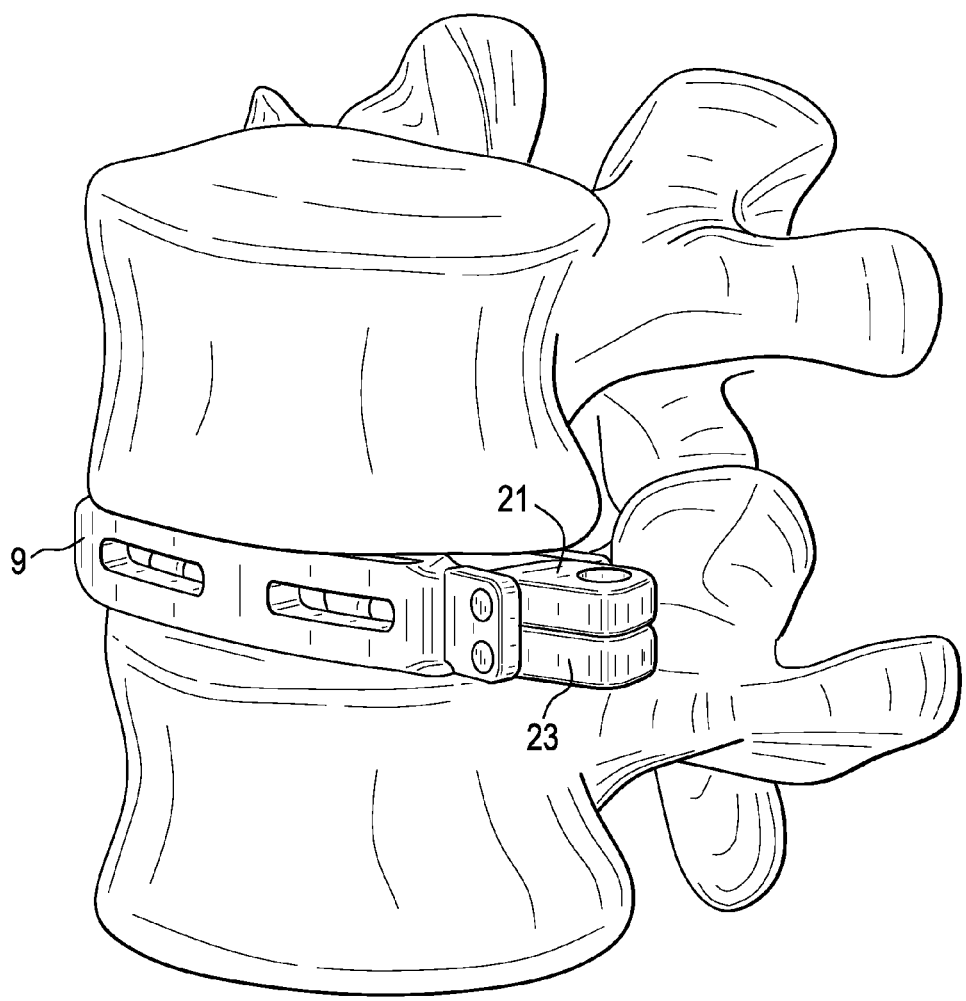
Figure 2F:
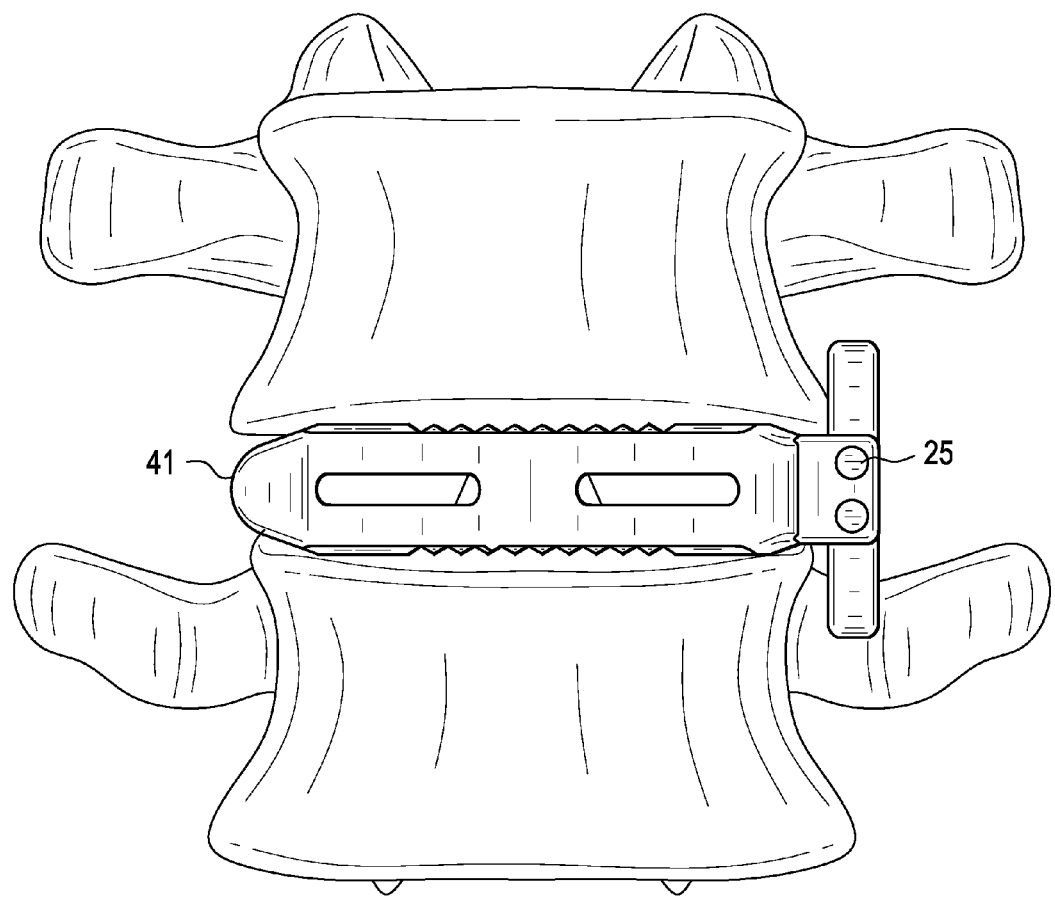
Figure 2G:
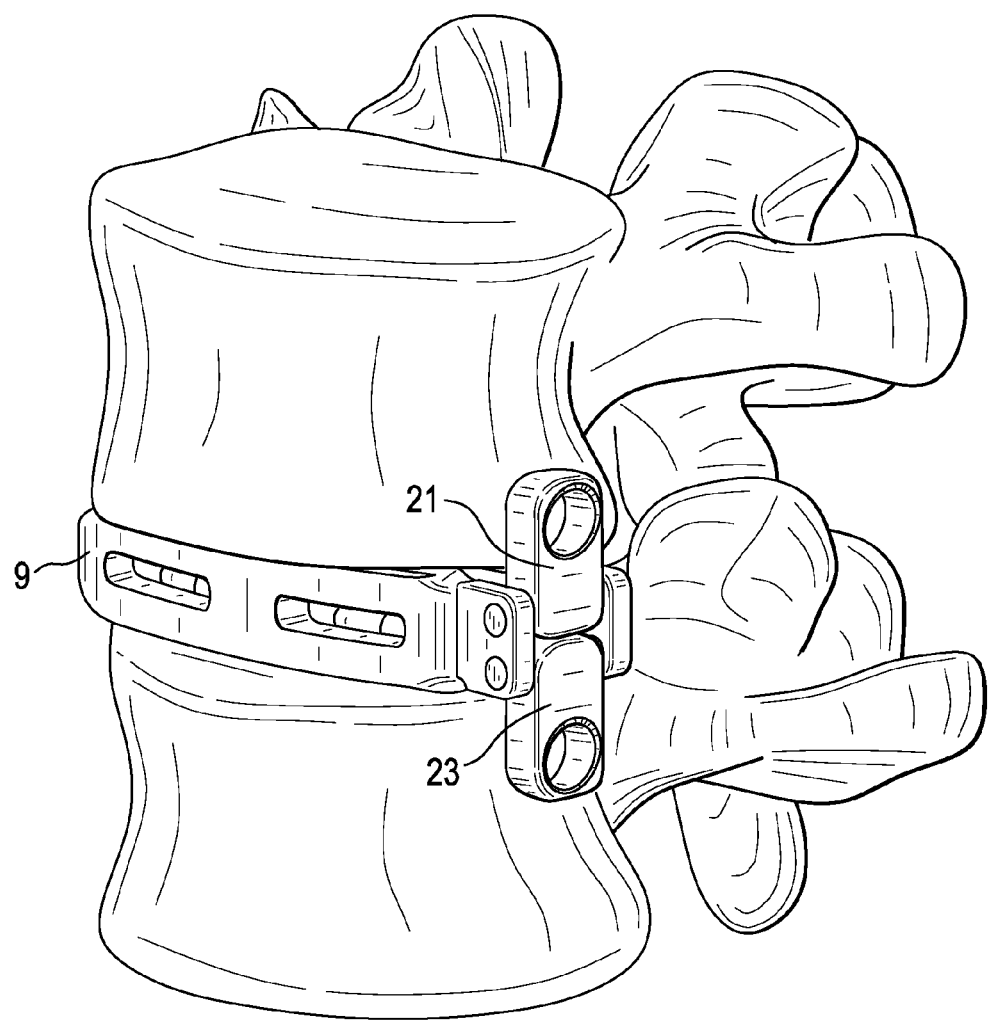
Figure 2H:
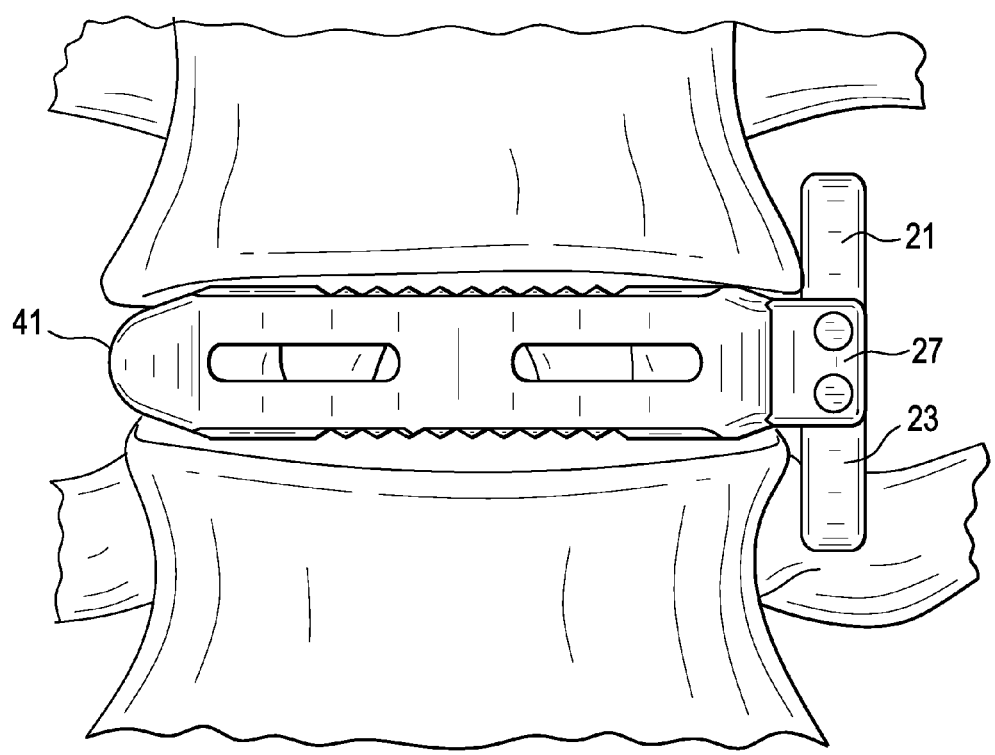
Figure 2I:
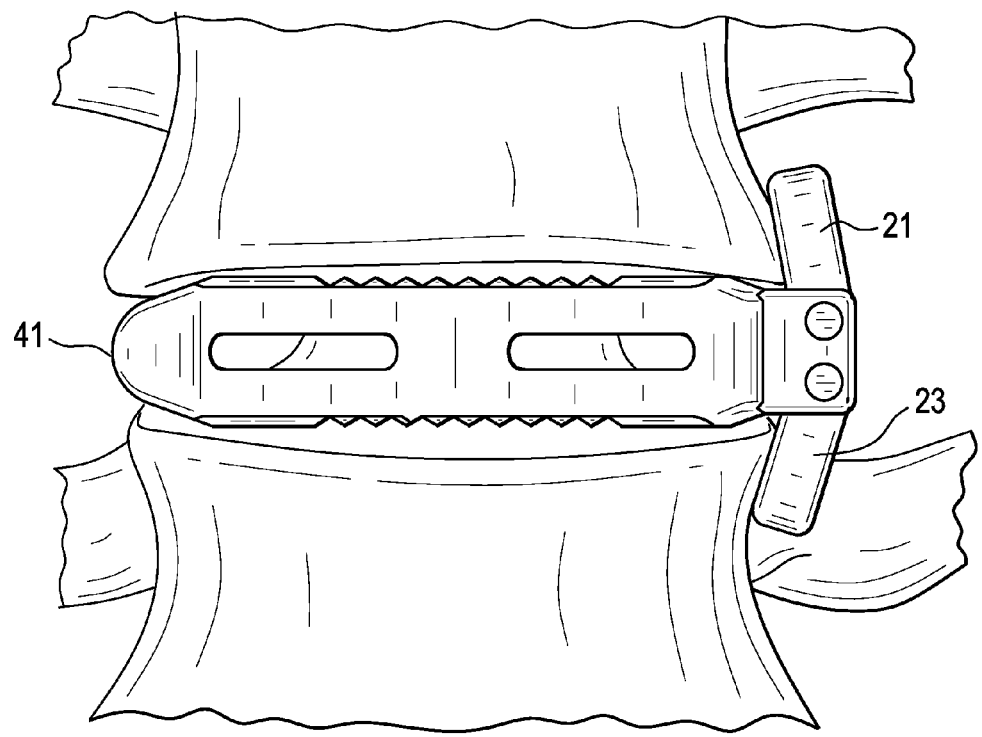

Now referring to FIGS. 2a-2i, the device of the present invention is inserted into a disc space as shown. Initially, when the device is outside of the disc space (and still in the portal), the device is in its closed (as shown in FIG. 2a). the closed configuration allows the device to pass through a minimally invasive portal. In a second phase, the device is inserted into the disc space in its closed configuration (as in FIGS. 2b, 2c, 2d, 2e,). In the third phase, with the cage fully in the disc space, the plates halves are spread apart to put the device in its open position. This is shown in FIGS. 2f, 2g, and 2h. Next, the opened device are contacted to the vertebral bodies, as in FIG. 2i.

In some embodiments, now referring to FIGS. 3a-4a, each plate half comprises a second end portion 35 having a screwhole 37. This through hole The surgeon may pass a screw through this screw-hole in order to secure the plate half to an adjacent vertebral body. Preferably, the device further comprises d) a plurality of screws 39 (such as two screws), wherein the screws are received in the screw-holes, thereby bilaterally securing the plate halves to the sides of the adjacent vertebral bodies.

Figure 3A:
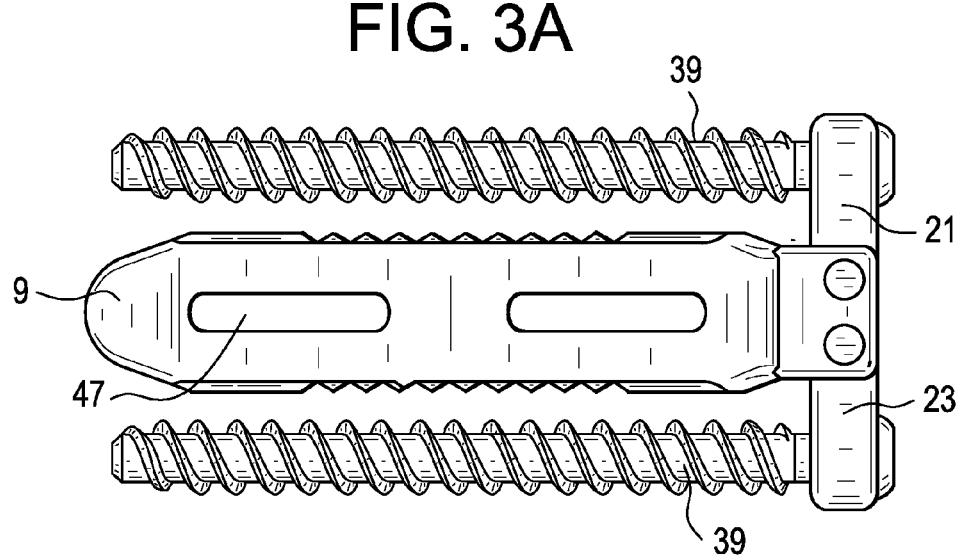
FIGS. 3a-3c disclose the device of the present invention with screws.
Figure 3B:
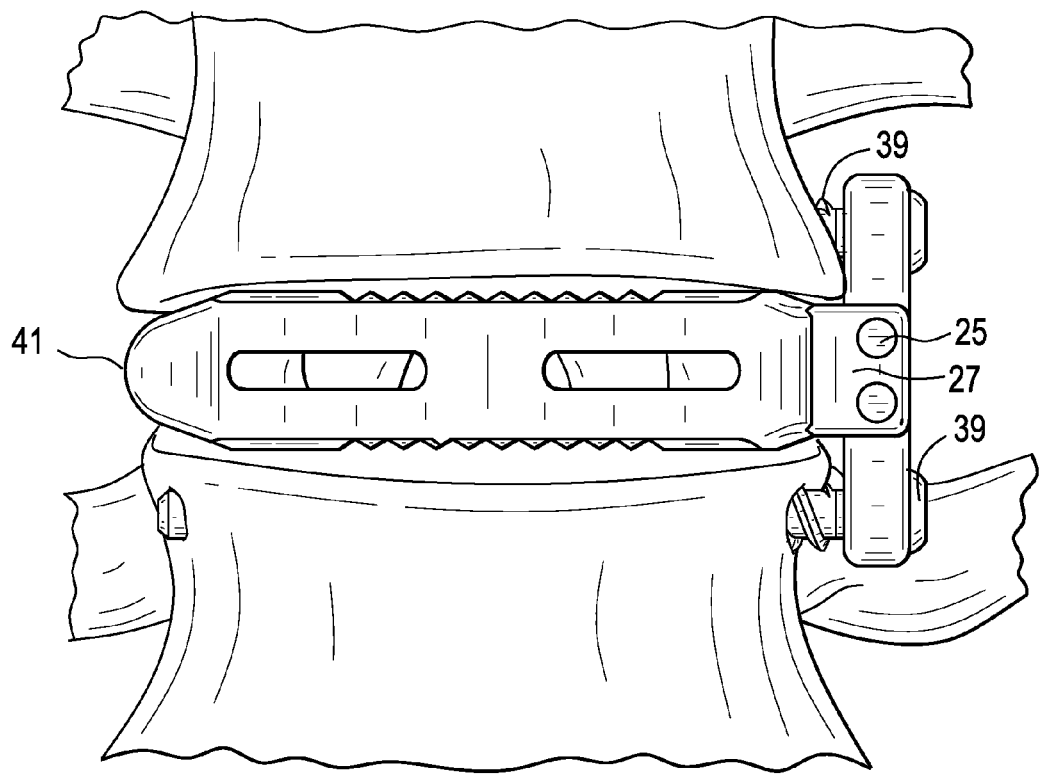
Figure 3C:
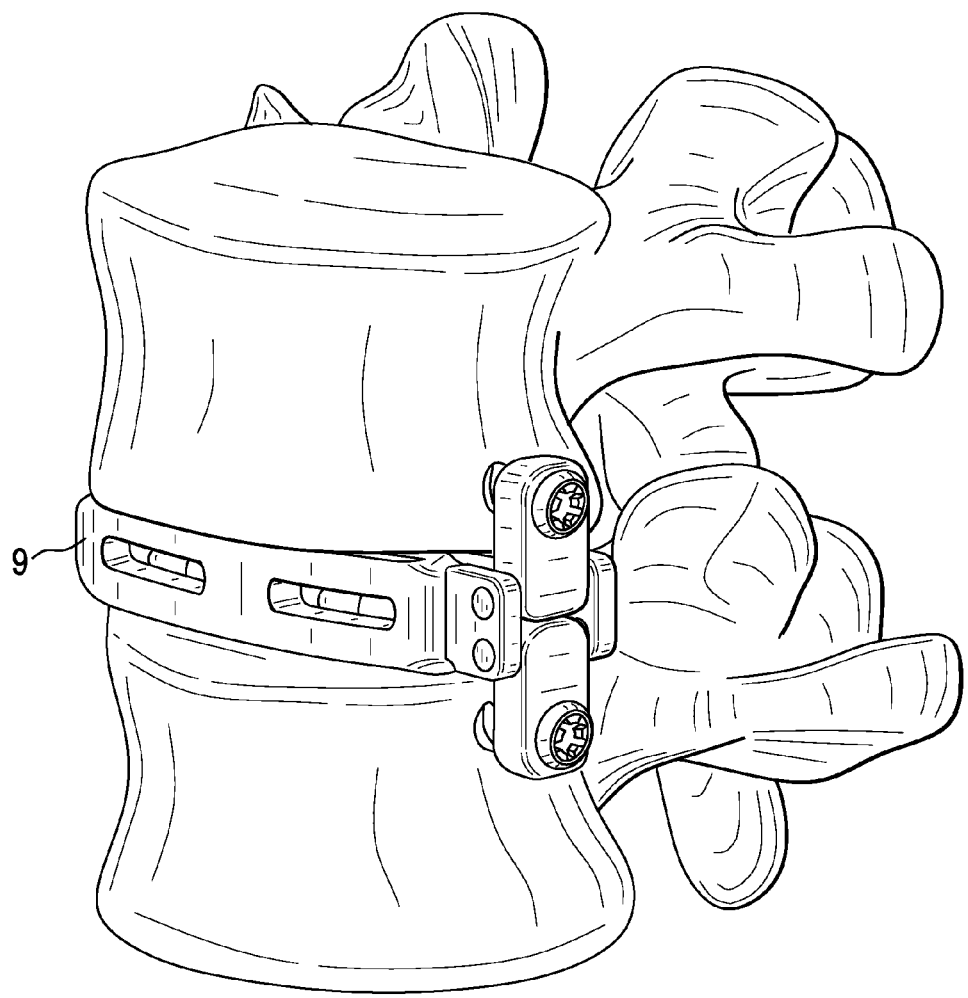

In the last phase of device insertion, the screws are passed through the inserted device and fix the device to the adjacent vertebral bodies. This is shown in FIGS. 3b and 3c.
In some embodiments, each screw comprises a lag feature.

In some embodiments, the device possesses features that are particularly suited to promote tissue sparing during a lateral approach. For example, in some embodiments, the anterior and posterior walls of the cage define a cage depth $D_C$, and the plate has a depth $D_P$, and the depth of the plate is not greater than the cage depth. This feature helps minimize the profile of the cage during insertion.

In some embodiments, the first side wall of the cage has a convex nose 41. This feature provides for ease of insertion of the cage into a disc space. In this embodiment, the flanges extend from the second side wall of the cage, and so are opposite the nose of the cage.

In some preferred embodiments, the sidewalls of the cage define a cage width $W_C$, and the width of the cage is at least two times the depth of the cage $D_C$. This geometric relation particularly points out the long, thin nature of lateral cages.

In some embodiments, the cage further has at least one strut 43 extending through the central throughhole from the anterior wall and the posterior wall so as to define at least two chambers 45 in the central throughhole. This is a common feature of lateral cages that allows for the tight packing of bone graft in the central throughhole.

In some embodiments, the anterior wall and the posterior wall of the cage each have at least one window 47 therein. These windows help promote bony fusion in and around the cage.

In some preferred embodiments, the cage has a height $H_C$, the plate halves have a closed position defining a first height $HC_{PH}$, and the height of the plate halves in the closed position is no more than the height of the cage. In these same embodiments, the plate halves have an open position to define have a second height $HO_{PH}$, and the second height of the plate halves in the open position is greater than the height of the cage. This highlights to the relatively small profile of the device in its closed position vis-à-vis the open position, and its utility in reducing the device profile.

In some embodiments, each plate half pivots in a plane substantially parallel to the anterior or posterior wall of the cage. This allows the plate half to be fixed to a sidewall of the adjacent vertebral body and pivot in the frontal plane.

In some embodiments, the upper and lower surfaces of the cage may be convex. Preferably, each is convex. The domed upper and lower surfaces provide a closer congruence with the normal anatomical concavity of the vertebral endplates than do their flat counterparts.

In some embodiments, the anterior wall of the cage is convex in order to more closely correspond with the curved anterior rim of the vertebral body.

In some embodiments, the upper and lower surface of the cage have teeth 101 for gripping the adjacent vertebral bodies (as shown in FIG. 1a).

In some embodiments, the device of the present invention comprises a single cross pin.

Figure 4A:
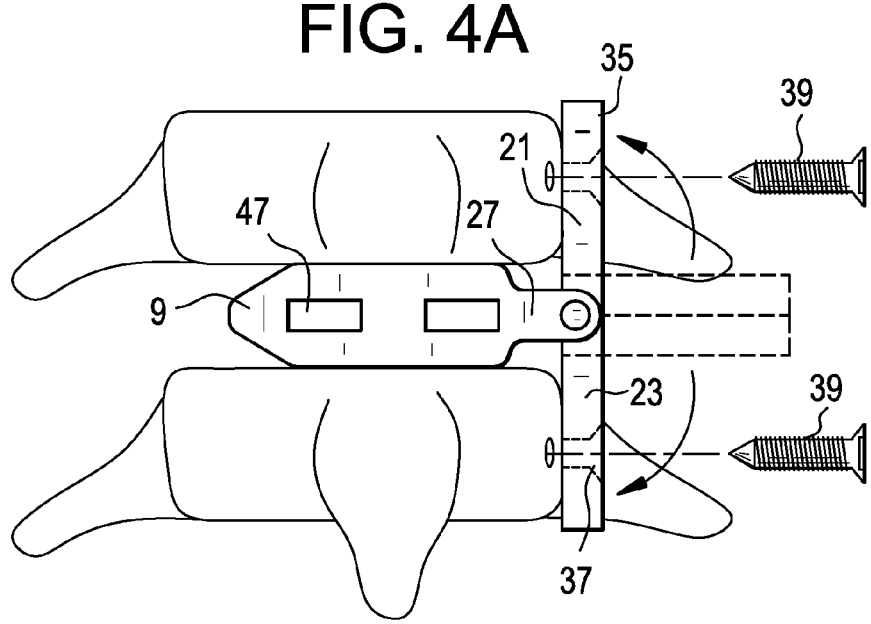
FIGS. 4a-4c disclose embodiments of the device having a single cross pin.
Figure 4B:
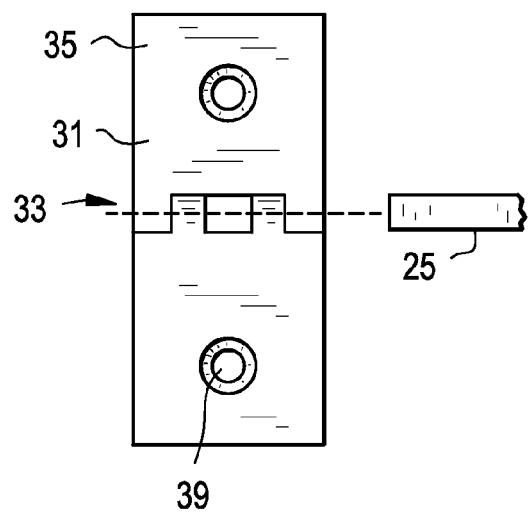
Figure 4C:
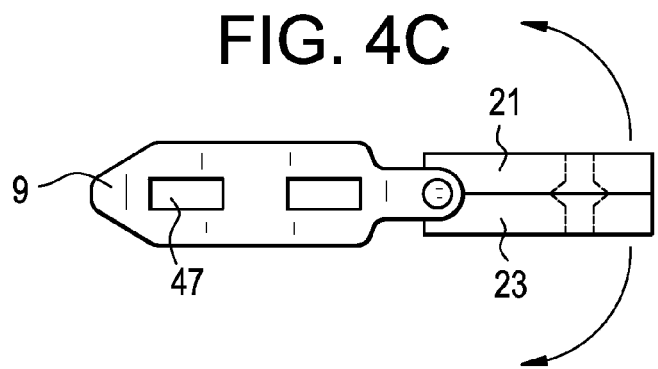

This embodiment is shown in FIG. 4a-4c. In this embodiment, each flange has one through hole 33. Thus, the device may further comprise:
c) a first pin 25,
wherein the cage further comprises a pair of flanges 27, each flange having a first throughhole, wherein the first throughholes are aligned, wherein the first and second plate halves each has a first end portion 31 having a throughhole 33, wherein the throughholes of each plate half are aligned, and wherein the first pin passes through the througholes of the flanges and the throughholes of the plate halves.

In some embodiments, a locking mechanism may be added to prevent rotation or micromotion once the plate halves are secured to the bone.

In some embodiments, there is provided a method of inserting the intervertebral fusion device of the present invention, comprising the steps of:
- a) inserting (preferably, either laterally or antero-laterally) the cage into a disc space with the plate halves in a closed configuration, and
- b) pivoting the plate halves into an open position.

Preferably, this method further comprises the step of c) securing the plate halves to the sides of adjacent vertebral bodies. Preferably, each plate half comprises a second end portion having a screwhole, and the securing step comprises passing a screw through each screw-whole and into a vertebral body.

In some embodiments, the insertion step takes place through a portal such as a cannula.

The cages of the present invention may be made from any non-resorbable material appropriate for human surgical implantation, including but not limited to, surgically appropriate metals, and non-metallic materials, such as carbon fiber composites, polymers and ceramics.

The interbody devices are preferably made out of PEEK or CFRP or any other suitable material providing adequate strength and radiolucency. However, implantable metals such as titanium or stainless steel components may be required to ensure adequate strength for either the interbody device. In some cases the interbody device can be made as a combination of PEEK and metal. In some cases, resorbable materials such as polylactide, polyglycolide, and magnesium are preferred.

In some embodiments, the cage material is selected from the group consisting of PEEK, ceramic and metallic. The cage material is preferably selected from the group consisting of metal and composite (such as PEEK/carbon fiber).

If a metal is chosen as the material of construction for a component, then the metal is preferably selected from the group consisting of titanium, titanium alloys (such as Ti-6Al-4V), chrome alloys (such as CrCo or Cr—Co—Mo) and stainless steel.

If a polymer is chosen as a material of construction for a component, then the polymer is preferably selected from the group consisting of polyesters, (particularly aromatic esters such as polyalkylene terephthalates, polyamides; polyalkenes; poly(vinyl fluoride); PTFE; polyarylethyl ketone PAEK; polyphenylene and mixtures thereof.

If a ceramic is chosen as the material of construction for a component, then the ceramic is preferably selected from the group consisting of alumina, zirconia and mixtures thereof. It is preferred to select an alumina-zirconia ceramic, such as BIOLOX Delta™, available from CeramTec of Plochingen, Germany.

In some embodiments, the cage member comprises PEEK. In others, it is a ceramic.

In some embodiments, the first component consists essentially of a metallic material, preferably a titanium alloy or a chrome-cobalt alloy.

In some embodiments, the components are made of a stainless steel alloy, preferably BioDur® CCM Plus® Alloy available from Carpenter Specialty Alloys, Carpenter Technology Corporation of Wyomissing, Pa. In some embodiments, the outer surfaces of the components are coated with a sintered beadcoating, preferably Porocoat™, available from DePuy Orthopaedics of Warsaw, Ind.

In some embodiments, the components are made from a composite comprising carbon fiber. Composites comprising carbon fiber are advantageous in that they typically have a strength and stiffness that is superior to neat polymer materials such as a polyarylethyl ketone PAEK. In some embodiments, each component is made from a polymer composite such as a PEKK-carbon fiber composite.

Preferably, the composite comprising carbon fiber further comprises a polymer.

Preferably, the polymer is a polyarylethyl ketone (PAEK). More preferably, the PAEK is selected from the group consisting of polyetherether ketone (PEEK), polyether ketone ketone (PEKK) and polyether ketone (PEK). In preferred embodiments, the PAEK is PEEK.

In some embodiments, the carbon fiber comprises between 1 vol % and 60 vol % (more preferably, between 10 vol % and 50 vol %) of the composite. In some embodiments, the polymer and carbon fibers are homogeneously mixed. In others, the material is a laminate. In some embodiments, the carbon fiber is present in a chopped state. Preferably, the chopped carbon fibers have a median length of between 1 mm and 12 mm, more preferably between 4.5 mm and 7.5 mm. In some embodiments, the carbon fiber is present as continuous strands.

In especially preferred embodiments, the composite comprises:
- 40-99% (more preferably, 60-80 vol %) polyarylethyl ketone (PAEK), and
- 1-60% (more preferably, 20-40 vol %) carbon fiber, wherein the polyarylethyl ketone (PAEK) is selected from the group consisting of polyetherether ketone (PEEK), polyether ketone ketone (PEKK) and polyether ketone (PEK).

In some embodiments, the composite consists essentially of PAEK and carbon fiber. More preferably, the composite comprises 60-80 wt % PAEK and 20-40 wt % carbon fiber. Still more preferably the composite comprises 65-75 wt % PAEK and 25-35 wt % carbon fiber.

In some embodiments, the pin component of the present invention is made from a biocompatible metal, such as stainless steel, chromium cobalt, or titanium alloy.

In some embodiments, the plate halves of the present invention are made from a biocompatible metal, such as stainless steel, chromium cobalt, or titanium alloy.

In some embodiments, the method of using the present invention is as follows:
Step 1: Assemble the cage/plate assembly to the inserter
Step 2: Insert the cage/plate assembly into the disc space
Step 3: Deploy open the plate (with either the inserter or a secondary instrument)
Step 4: Drill and tap holes through the plate
Step 5: Insert bone screws
Step 6: Tighten the locking mechanism In some embodiments, the central throughhole of the cage is filled with a fusion material. This fusion material promotes bony fusion of the adjacent vertebral bodies through the disc space. In some embodiments, the fusion material may be autograft bone marrow or allograft bone. In some embodiments, the fusion material may be synthetic, such as tricalcium phosphate or hydroxyapatite. In some embodiments, the fusion material may be a recombinant protein, such as a growth factor.

Although the present invention has been described with reference to its preferred embodiments, those skillful in the art will recognize changes that may be made in form and structure which do not depart from the spirit of the invention.

I claim:
1. An intervertebral fusion device comprising:
a) an intervertebral fusion cage having an anterior wall, a posterior wall, first and second side walls connecting the anterior and posterior walls to form a central through- hole, an upper surface adapted for gripping an upper endplate and a lower surface adapted for gripping a lower endplate; and b) a plate comprising first and second halves,
wherein each half of the plate is pivotally connected to the cage,
c) a first pin,
wherein the cage further comprises a pair of flanges, each flange having a first throughhole,
wherein the first pin passes through the througholes of the flanges,
wherein the first side wall has a convex nose adapted to ease insertion of the cage into a disc space, and
wherein the flanges extend from the second side wall of the cage.

2. The device of claim 1
wherein the first throughholes are aligned, wherein the first and second plate halves each has a first end portion having a throughhole, wherein the throughholes of each plate half are aligned, and
wherein the first pin passes through the throughholes of the plate halves.

3. The device of claim 2 wherein each plate half comprises a second end portion having a screwhole, and wherein the device further comprises:
d) a pair of screws, wherein the screws are threadably received in the screwholes.

4. The device of claim 1 further comprises
c) first and second pins,
wherein the cage further comprises a pair of flanges, each flange having a first and second throughhole, wherein the first throughholes are aligned and wherein the second throughholes are aligned, wherein the first and second plate halves each has a first end portion having a throughhole,
wherein the first pin passes through the first througholes of the flanges and the throughhole of the first plate half,
wherein the second pin passes through the second througholes of the flanges and the throughhole of the second plate half.

5. The device of claim 1 wherein the anterior and posterior walls of the cage define a cage depth, and the plate has a depth, wherein the depth of the plate is not greater than the cage depth.

6. The device of claim 4 wherein each screw comprises a lag feature.

7. The device of claim 1 wherein the cage has a width and a depth, and the width of the cage is at least two times the depth of the cage.

8. The device of claim 1 wherein the cage further has at least one strut extending from the anterior wall to the posterior wall so as to define at least two chambers in the central throughhole.

9. The device of claim 1 wherein the anterior wall and the posterior wall of the cage each have at least one window therein.

10. The device of claim 1 wherein the cage has a height, wherein the plate halves in a closed position define a first height, and wherein the height of the plate halves in the closed position is no more than the height of the cage.

11. The device of claim 1 wherein the cage has a height, wherein the plate halves in an open position define have a second height, wherein the second height of the plate halves in the open position is greater than the height of the cage.

12. The device of claim 1 wherein the plate pivots in a plane substantially parallel to the posterior wall of the cage.

13. A method of inserting an intervertebral fusion device comprising:
i) an intervertebral fusion cage having an anterior wall, a posterior wall, first and second side walls connecting the anterior and posterior walls to form a central throughhole, an upper surface adapted for gripping an upper endplate and a lower surface adapted for gripping a lower endplate; and
ii) a plate comprising first and second halves,
wherein each half of the plate is pivotally connected to the cage,
comprising the steps of:
a) laterally inserting the device into a disc space with the plate halves in a closed configuration,
b) pivoting the plate halves into an open position.

14. The method of claim 13 further comprising the step of:
c) securing the plate halves to adjacent vertebral bodies.

15. The method of claim 14 wherein each plate half comprises a second end portion having a screwhole, and the securing step comprises passing a screw through each screwhole and into a vertebral body.

16. The method of claim 13 wherein the insertion step takes place through a portal.

17. The method of claim 13 wherein the pivoting causes each plate to contact a respective sidewall of an adjacent vertebral body.

* * * * *